United States Patent [19]

Fuller et al.

[11] Patent Number: 5,277,870
[45] Date of Patent: *Jan. 11, 1994

[54] BLOOD GLUCOSE REFLECTANCE METER INCLUDING A NULL PROMPTING MEANS AND A DEVICE FOR PROVIDING A CONSTANT BRIGHTNESS LIGHT

[75] Inventors: Maurice D. Fuller; Richard A. Riedel, both of Carmel, Ind.

[73] Assignee: United Medical Manufacturing Company, Indianapolis, Ind.

[*] Notice: The portion of the term of this patent subsequent to Dec. 29, 2009 has been disclaimed.

[21] Appl. No.: 929,168

[22] Filed: Aug. 11, 1992

Related U.S. Application Data

[63] Continuation-in-part of Ser. No. 638,170, Jan. 7, 1991, Pat. No. 5,174,963.

[51] Int. Cl.$^5$ .......................................... G01N 21/77
[52] U.S. Cl. ............................. 422/82.05; 422/82.12; 422/56; 436/95; 436/169; 250/238; 356/446
[58] Field of Search ............... 422/56, 68.1, 82.01, 422/82.02, 82.05, 82.12; 436/95, 169; 356/446; 250/238

[56] References Cited

U.S. PATENT DOCUMENTS

| | | | |
|---|---|---|---|
| 3,907,503 | 9/1975 | Betts et al. | 422/67 |
| 4,797,256 | 1/1989 | Watlington, IV | 422/58 |
| 4,871,258 | 10/1989 | Herpichboehm et al. | 356/422 |
| 4,895,444 | 1/1990 | Miyata et al. | 356/128 |
| 4,917,500 | 4/1990 | Lugos | 356/406 |
| 5,029,277 | 7/1991 | Kane | 250/214 C |
| 5,057,275 | 10/1991 | Neuman | 422/55 |
| 5,132,086 | 7/1992 | Allen et al. | 422/56 |
| 5,174,963 | 12/1992 | Fuller et al. | 422/56 X |
| 5,179,005 | 1/1993 | Phillips et al. | 422/56 X |

FOREIGN PATENT DOCUMENTS 3026439 2/1982 Fed. Rep. of Germany.

Primary Examiner—James C. Housel
Assistant Examiner—Maureen M. Wallenhorst
Attorney, Agent, or Firm—Woodard, Emhardt, Naughton, Moriarty & McNett

[57] ABSTRACT

A portable blood chemistry monitoring meter that employs an analog circuit in conjunction with a manually adjustable potentiometer to locate a null position that balances the measure taken of the blood chemistry-induced changes in the chemistries of disposable test strips. The meter displays in pre-printed, man-readable format blood chemistry concentrations that are individually calibrated to the specific batch-lot chemistries of the disposable test strips used with the meter. In a preferred embodiment, the meter is a blood glucose monitoring meter.

18 Claims, 4 Drawing Sheets

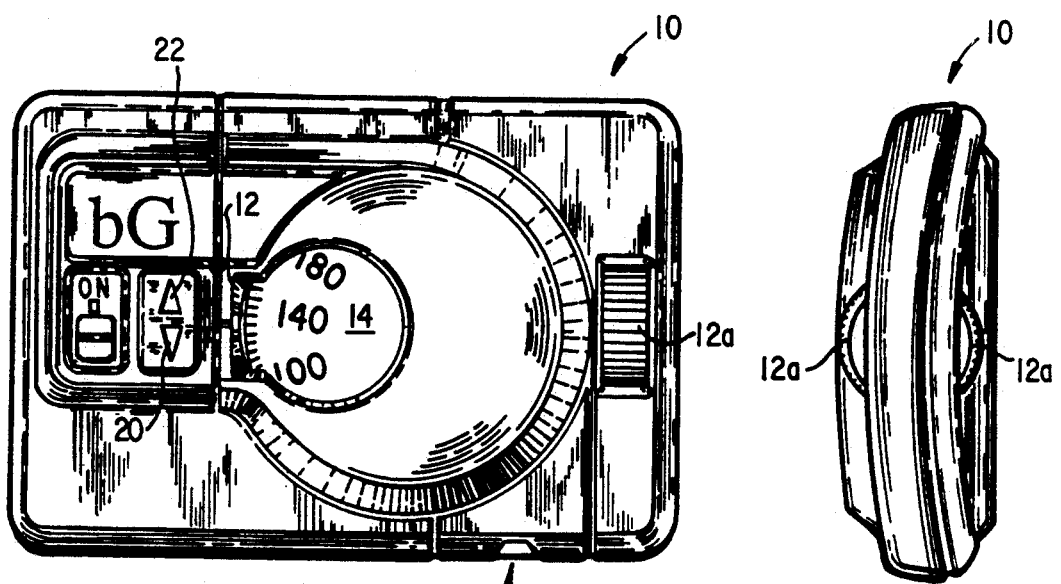
Fig.1
Fig.2
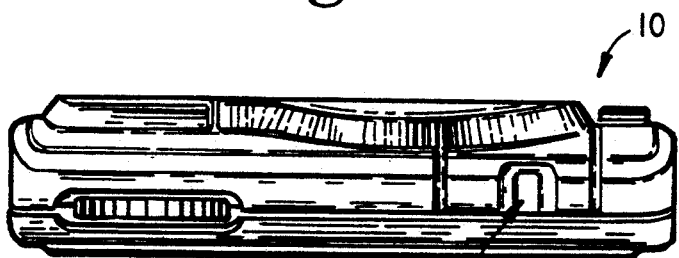
Fig.3
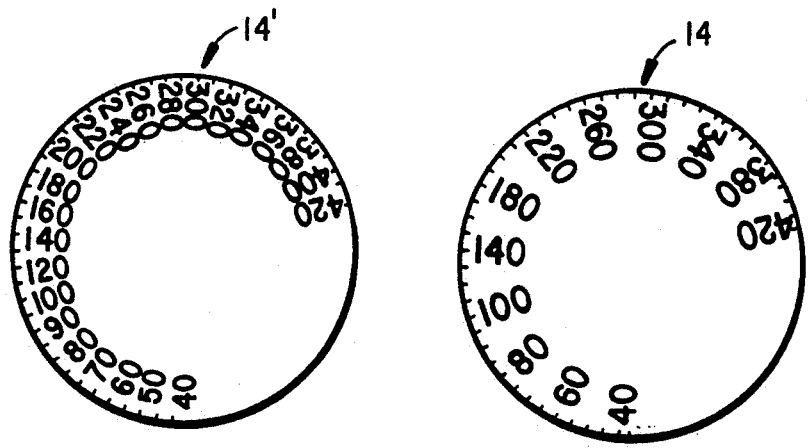
Fig.5
Fig.4

BLOOD GLUCOSE REFLECTANCE METER INCLUDING A NULL PROMPTING MEANS AND A DEVICE FOR PROVIDING A CONSTANT BRIGHTNESS LIGHT

REFERENCE TO RELATED APPLICATIONS

This application is a continuation-in-part of U.S. patent application Ser. No. 07/638,170, filed on Jan. 7, 1991, now U.S. Pat. No. 5,174,963, issued Dec. 29, 1992.

BACKGROUND OF THE INVENTION

The invention relates generally to blood chemistry monitoring utilizing enzyme-based blood analysis systems, such as blood glucose or cholesterol systems, and more specifically to portable blood chemistry monitoring meters for use with enzyme-based blood analysis systems.

Portable blood glucose monitoring meters were first made available for use in the late 1970's. Portable meters provided patients and health care providers with the means to improve insulin control by permitting them to determine blood glucose levels quickly and with reasonable accuracy, without the need for vein puncture and laboratory analysis. Since the introduction of such meters, improvements to date have produced portable meters offering greater convenience in smaller sizes with more features.

Portable blood glucose monitoring meters today typically utilize disposable test strips, similar to litmus paper, that have applied chemistries that either produce a color change or a change in electrical resistance when a drop of a patient's capillary blood is applied to the chemistries. In the case of test strips with chemistries that produce a color change, the strip becomes darker in proportion to the amount of blood glucose present in the blood. In such cases, the strip bearing the patient's blood is inserted into the meter and the color change in the chemistry on the strip is measured using an optical reflectance system within the meter. A microprocessor-based program within the meter then processes the color change measurement and generates a digital readout of the corresponding concentration, typically in milligrams per milliliter, of blood glucose in the patient's capillary blood. Such meters are commonly known as reflectance meters, and they are the most common type of portable blood glucose monitoring meter in use today.

In the case of test strips with applied chemistries that change in electrical resistance when a drop of a patient's capillary blood is applied to the chemistries, the change in electrical resistance is proportional to the concentration of blood glucose in the blood. In such cases, the strip is inserted into the meter and the change in electrical resistance is measured by the meter. A microprocessor-based program within the meter then processes the electrical resistance measurement and generates a digital readout of the corresponding concentration in milligrams per milliliter of blood glucose in the patient's capillary blood. Such meters are the least common type of portable blood glucose monitoring meters in use today.

In addition to generating digital readouts of blood glucose concentrations, another key function of the microprocessors found in all portable blood glucose monitoring meters in use today is the application of empirically derived correction factors to account for slight variations in the chemistries applied to test strips at the time of manufacture. Test strips are manufactured in batch lots. There is invariably slight lot-to-lot variations in the chemistries applied to test strips due to the complexities of the chemistries involved. It is therefore necessary to calibrate all portable blood glucose monitoring meters in use today to account for such lot-to-lot variations to assure consistent and accurate relationships between the color or resistance changes in such chemistries as measured by the meters and the corresponding blood glucose concentrations generated by the meter's microprocessor.

Lot-specific calibration factors for test strips are empirically derived by the test strip manufacturers. The lot specific calibration factors then accompany each package of test strips in a format that is suitable for use in a particular meter model. This has been accomplished to date in several different ways.

In one case, a bar code reader is provided in the meter. Lot-specific correction factors are provided with each package of test strips in a bar code format that can be read into the meter's microprocessor through the meter's bar code reader. Another method requires that a lot-specific code number be entered into the meter's microprocessor using keys located on the meter. The code number calls up a particular correction curve that has been programmed into the meter's microprocessor. Yet another method provides an electronic module with each package of test strips that is inserted into a receiving socket on the meter. The module houses an electronic memory element that contains the lot-specific correcting information for the meter's microprocessor.

Whatever the precise method utilized to enter the lot-specific correction factors into the meter's microprocessor, the microprocessor applies the lot-specific correction factors to the measurements taken by the meter of the blood glucose-induced changes in test strip chemistries, and then generates a corrected digital readout of the patient's capillary blood glucose concentration.

The drive to reduce the manufacturing costs of portable blood glucose monitoring meters led to a review of the foregoing methods of determining blood glucose concentrations. It was found that all portable blood glucose monitoring meters in use today have a common minimum manufacturing cost factor: the lower limit is determined by the cost of the microprocessor and the microprocessor-based electronic circuitry. Efforts to reduce the cost to patients of portable blood glucose monitoring meters are therefore impeded by the fixed costs of microprocessors and their related electronic circuitry.

The portable blood chemistry monitoring meters of the present invention employ a different and less expensive approach to enzyme-based blood analysis through measurements taken of the blood-induced changes in the chemistries of disposable test strips. The meters of the present invention provide a patient-operated devices that feature man-readable, replaceable, lot-specific calibration means to account for the lot-to-lot variation in test strip chemistries without the use of a microprocessor in one embodiment, and man-readable, individually calibrated, disposable test strips in yet another embodiment. The meters of the present invention therefore employ a more simple and less costly approach to enzyme-based blood analysis than is employed in any of the portable blood chemistry monitoring meters in use today.

SUMMARY OF THE INVENTION

The portable blood chemistry monitoring meter of one of the preferred embodiments of the invention is a blood glucose monitoring meter. This preferred embodiment employs an analog circuit in conjunction with a manually rotatable dial that varies the resistance of a potentiometer to locate a null position that balances the measure taken of the blood glucose-induced changes in the chemistries of disposable test strips of the prior art. The dial supports a replaceable, pre-printed calibration disk. The calibration disk displays in man-readable format blood glucose concentrations in milligrams per milliliter that have been calibrated to the specific batch-lot chemistries of the disposable test strips used with the meter. A patient places a replaceable calibration disk upon the dial, and inserts a corresponding test strip bearing a drop of the patient's capillary blood into the meter. The patient then manually adjusts the dial until prompting arrows indicate a null position. If the dial has rotated past the null position, an opposing arrow will illuminate indicating a need to rotate the dial in the opposite direction. The procedure is repeated until a null position is found. At the null position, the prompting arrows illuminate simultaneously, or a third indicator is illuminated. The calibrated concentration of the patient's blood glucose in milligrams per milliliter is then read directly from the number appearing on the calibration disk at the null point. The concentration of blood glucose is interpolated in a manner similar to reading a common thermometer.

Another preferred embodiment of the portable blood chemistry monitoring meter of the invention is also a blood glucose monitoring meter that employs an analog circuit in conjunction with a manually sliding pointer that adjusts the resistance of a potentiometer to locate a null position that balances the measure taken of the blood glucose-induced changes in the chemistries of disposable test strips. In this embodiment, printed or otherwise impressed directly on the disposable test strip itself is a man-readable, individually calibrated, graduated scale of blood glucose concentrations in milligrams per milliliter. This scale has been individually calibrated to the specific hatch-lot chemistries applied to the test strip upon which the scale is printed or impressed by the test strip manufacturer at the time of manufacture. In this embodiment, a patient inserts the test strip bearing a drop of the patient's capillary blood into the meter, and the disposable test strip is registered into a precise position within the meter with the graduated scale of blood glucose concentration in juxtaposition with the sliding pointer of the meter. The patient then manually adjusts the sliding pointer until a null position is located, indicated, for example, by the illumination of an indicator light. The calibrated concentration of the patient's blood glucose in milligrams per milliliter may then read directly from the number appearing on the graduated scale of the test strip opposite the sliding pointer. Again, the concentration of blood glucose is interpolated in a manner similar to reading a common thermometer.

The basic principles of the portable blood glucose monitoring meters of the preferred embodiments of the invention are well known. Early blood glucose measuring instruments utilized analog circuitry and were manufactured using the basic principles underlying the preferred embodiments of the meters of the invention. However, the replaceable, man-readable, calibrated disk and the non-linear null prompting concepts of the first mentioned preferred embodiment, and the man-readable, individually calibrated disposable test strip bearing a printed or impressed graduated scale of blood chemistry concentrations of the second mentioned preferred embodiment of the present invention were not employed. The features of the portable blood glucose monitoring meters of the preferred embodiments of the invention not found in the prior art include the ability to provide inexpensive means to calibrate disposable test strip batch lot chemistries with a replaceable, man-readable calibration disk, or with man-readable, individually calibrated blood chemistry concentrations printed or imprinted directly upon the disposable test strips in a graduated scale format; the non-linear null prompting system of the first-mentioned preferred embodiment; and the innovative circuitry to be described that provides novel optical reflectance system features; all without the use of microprocessors. No portable blood glucose monitoring meter in use today incorporates either a manually operated dial that features a replaceable man-readable calibration disk with a non-linear null prompting system, as summarized; or a disposable test strip with man-readable, individually calibrated blood chemistry concentrations printed or impressed directly upon the disposable test strip in a graduated scale format.

Another preferred embodiment of the present invention is a portable blood glucose monitoring meter having an analog circuit with a variable potentiometer to measure blood glucose-induced changes in the chemistries of disposable test strips to determine blood glucose concentrations, the improvements comprising dial means to vary manually the resistance of the potentiometer to locate a null position that balances the measure of the blood glucose-induced changes in the chemistries of disposable test strips, and calibration means integral with the dial means to receive replaceable, pre-printed, man-readable blood glucose concentrations that correspond to the null positions located by the dial means and that are empirically calibrated to the batch lot variations in the chemistries of the disposable test strips used in the meter.

Yet another preferred embodiment of the present invention is a method of determining blood glucose concentrations, comprising the steps of providing a portable blood glucose monitoring meter having an analog circuit with a variable potentiometer to measure blood glucose-induced changes in the chemistries of disposable test strips to determine blood glucose concentrations, a manually rotatable dial to vary the resistance of the potentiometer to locate a null position that balances the measure of the blood glucose-induced changes in the chemistries of disposable test strips, calibration means integral with the dial to receive a replaceable, pre-printed calibration disk containing blood glucose concentrations that correspond to the null positions located by the dial and that are empirically calibrated to the batch lot variations in the chemistries of the disposable test strips used in the meter, and null prompting means to indicate the manual variation of the dial means required to achieve a null position, positioning on the dial a replaceable, pre-printed, man-readable calibration disk containing blood glucose concentrations corresponding to the null positions located by the dial that are empirically calibrated to the chemistries of disposable test strips to be used in the meter, inserting a test strip bearing chemistry calibrated to the calibration disk and with a drop of capillary blood thereon into the meter, rotating the dial manually until the null prompting means indicates a null position, and reading directly from the calibration disk at the null position the concentration of blood glucose present in the capillary blood.

Yet another preferred embodiment of the present invention is a portable blood glucose monitoring meter having an analog circuit with a variable potentiometer and a reflectance measuring system to measure blood glucose-induced color changes in the chemistries of disposable test strips to determine blood glucose concentrations, the improvements comprising a light emitting diode as the light source within the reflectance measuring system, and first circuit means connected to the light emitting diode for providing a current signal to the light emitting diode that varies in accordance with variations in ambient temperature to maintain a constant intensity brightness signal from the light emitting diode.

Yet another preferred embodiment of the present invention is a device for providing a constant brightness light signal, comprising temperature compensation means for producing a temperature compensating signal, power source means responsive to the temperature compensating signal for producing a power signal in accordance with the temperature signal, and a light emitting diode responsive to the power signal and producing a constant intensity light signal in response thereto.

Yet another preferred embodiment of the present invention is a portable blood chemistry monitoring meter having an analog circuit with a variable potentiometer to measure blood chemistry-induced changes in an enzyme-based blood analysis system utilizing disposable test strips to determine blood chemistry concentrations, the improvements comprising dial means to vary manually the resistance of the potentiometer to locate a null position that balances the measure of the blood chemistry-induced changes in the chemistries of the disposable test strips, and calibration means integral with the dial means to receive replaceable, pre-printed, man-readable blood chemistry concentrations that correspond to the null positions located by the dial means and that are empirically calibrated to the batch lot variations in the chemistries of the disposable test strips used in the meter.

Yet another preferred embodiment of the present invention is a portable blood glucose monitoring meter having an analog circuit with a variable potentiometer to measure blood glucose-induced changes in the chemistries of disposable test strips to determine blood glucose concentrations, the improvements comprising a sliding pointer with means to vary manually the resistance of the potentiometer to locate a null position that balances the measure of the blood glucose-induced changes in the chemistries of disposable test strips, and slot means to receive disposable test strips bearing calibration means that will be in registered juxtaposition with the sliding pointer when received by the slot means, the calibration means including man-readable blood glucose concentrations that correspond to the null positions located by the sliding pointer and that have been empirically calibrated to the batch lot variations in the chemistries of the disposable test strips.

Yet another preferred embodiment of the present invention is a method of determining blood glucose concentrations, comprising the steps of providing a portable blood glucose monitoring meter having an analog circuit with a variable potentiometer to measure blood glucose-induced changes in the chemistries of disposable test strips to determine blood glucose concentrations, a sliding pointer to vary the resistance of the potentiometer to locate a null position that balances the measure of the blood glucose-induced changes in the chemistries of disposable test strips, slot means to receive disposable test strips bearing calibration means that will be in juxtaposition with the sliding pointer when received by the slot means, the calibration means including man-readable blood glucose concentrations that correspond to the null positions located by the sliding pointer and that have been empirically calibrated to the batch lot variations in the chemistries of the disposable test strips; inserting into the slot means a test strip bearing chemistries that have been empirically calibrated to man readable blood glucose concentrations pre-printed on the test strip until the concentrations are in registered juxtaposition with the sliding pointer, sliding the pointer manually until a null position is reached, and reading directly from the pre-printed blood glucose concentrations at the null position the concentration of blood glucose present the capillary blood appearing opposite the pointer.

Yet another preferred embodiment of the present invention is a portable blood chemistry monitoring meter having an analog circuit with a variable potentiometer to measure blood chemistry-induced changes in an enzyme-based blood analysis system utilizing disposable test strips to determine blood chemistry concentrations, the improvements comprising a sliding pointer with means to vary manually the resistance of the potentiometer to locate a null position that balances the measure of the blood chemistry-induced changes in the chemistries of disposable test strips, and slot means to receive disposable test strips bearing calibration means that will be in registered juxtaposition with the sliding pointer when received by the slot means, the calibration means including man-readable blood chemistry concentrations that correspond to the null positions located by the sliding pointer and that have been empirically calibrated to the batch lot variations in the chemistries of the disposable test strips.

Yet another preferred embodiment of the present invention is a disposable test strip for a portable blood chemistry monitoring meter having an analog circuit with a variable potentiometer to measure blood chemistry-induced changes in an enzyme-based blood analysis system applied to the test strip to determine blood chemistry concentrations, the improvements comprising calibration means to calibrate the batch lot variations in the chemistries of the enzyme-based blood analysis system in a man-readable format, including pre-printed, man-readable blood chemistry concentrations registered directly on the test strip in positions corresponding to blood chemistry concentrations located by empirical testing with known blood chemistry concentrations.

It is an object of the present invention to provide a less costly portable blood chemistry monitoring meter for enzyme-based blood analysis systems, such as blood glucose or cholesterol.

It is a further object of the present invention to provide a portable blood chemistry monitoring meter that eliminates the need for costly microprocessors and microprocessor-based electronic circuitry, thereby lowering the cost of portable blood chemistry monitoring meters according to the invention.

It is a further object of the present invention to provide a portable blood chemistry monitoring meter without a microprocessor or microprocessor-based electronic circuitry to incorporate lot-specific correction factors for disposable test strips.

It is a further object of the invention to provide a portable blood chemistry monitoring meter with a null prompting system to assist patients in locating a null position.

It is a further object of the invention to provide a portable blood chemistry monitoring meter with a temperature-based current compensation for a light emitting diode used in the optical reflectance measuring system utilized in a preferred embodiment of the portable blood chemistry monitoring meter of the invention that does not require a microprocessor.

It is a further object of the invention to provide disposable test strips for enzyme-based blood analysis systems with man-readable, individually calibrated blood chemistry concentrations printed or impressed directly on the disposable test strips in a graduated scale format, calibrated to the batch lot chemistries applied to the test strips.

Related objects and advantages of the portable blood glucose monitoring meter of the present invention will be evident from the following description.

BRIEF DESCRIPTION OF THE DRAWINGS

FIG. 1 is a top plan view of one embodiment of a portable blood glucose monitoring meter of a preferred embodiment of the invention.

FIG. 2 is a right side view of the portable blood glucose monitoring meter of FIG. 1.

FIG. 3 is a front elevational view of the portable blood glucose monitoring meter of FIG. 1.

FIG. 4 is a top plan view of one embodiment of the replaceable calibration disk utilized in the portable blood glucose monitoring meter of FIG. 1.

FIG. 5 is a top plan view of another embodiment of the replaceable calibration disk utilized in the portable blood glucose monitoring meter of FIG. 1.

DESCRIPTION OF THE PREFERRED EMBODIMENTS

Figure 6:
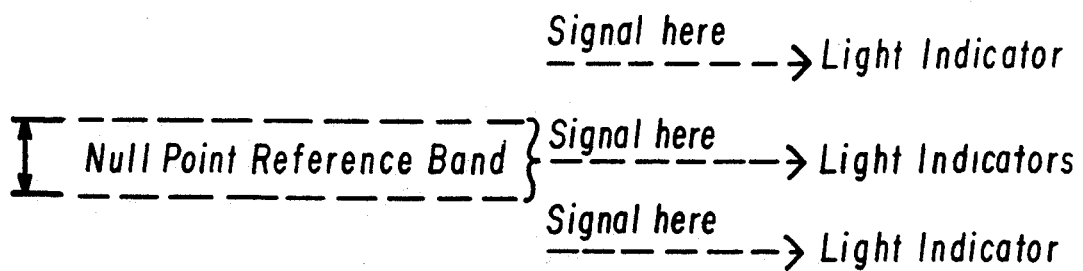
FIG. 6 is a diagram illustrating the operation of the non-linear null prompting system of the portable blood glucose monitoring meter of the invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

Referring now to the drawings, there is shown in FIGS. 1-8 one of the preferred embodiments of the invention, a portable blood glucose monitoring meter 10. Meter 10 employs an analog circuit in conjunction with a manually rotatable dial 12, rotated by adjustment knob 12a, to vary the resistance of a potentiometer to balance the measure of the blood glucose-induced changes in the chemistries of the disposable test strips of the prior art to be utilized in the meter 10. Dial 12 receives and supports a replaceable, pre-printed calibration disk 14 (FIG. 4). On the face of disk 14 are blood glucose concentration numbers in milligrams per milliliter of blood in a man-readable format. The numbers are calibrated, by their positioning about the periphery of disk 14, by empirical data to correspond to the specific batch lot variations in the chemistries of the disposable test strips to be used with the meter. A calibrated disk, such as disk 14 of FIG. 4, or disk 14' of FIG. 5, is created by the test strip manufacturer for each batch lot of test strips manufactured by testing the disposable test strips from each batch lot with a meter 10 to locate null positions at reference blood glucose concentrations. An exact duplicate of disk 14 (or 14') is then included in each package of test strips sold from the batch lot.

When a patient first opens a new package of disposable test strips, the calibration disk 14 accompanying the package would be removably affixed to dial 12 by a surface adhesive or the like. The face of meter 10 of FIG. 1 opens above dial 12 to allow access to the full face of circular dial 12 of the preferred embodiment to place disk 14 in a pre-registered orientation upon the face of dial 12 and/or to remove a prior calibration disk 14 from a previous package of test strips. The patient would then apply a drop of capillary blood to the chemistry of a test strip corresponding to the calibration disk 14, and then insert the test strip bearing the blood into meter 10 at test strip inlet 18.

The patient then rotates dial 12, until the prompting arrows 20 and 22 indicate a null position. If the dial 12 has rotated past the null position, the opposing arrow 20 or 22 will illuminate indicating a need to rotate the dial 12 in the opposite direction. The procedure is repeated until a null position is found. At the null position, a third indicator may be incorporated (not shown) to indicate that the null position has been reached. Alternatively, the two prompting arrows 20 and 22 may illuminate simultaneously, as would be the case in the preferred embodiment shown in FIG. 1, as an indication that a null position has been reached, thus eliminating the need for a third indicator. The indicator arrows 20 and 22 may be light emitting diodes, liquid crystal display icons, incandescent lamps, or other means such as electromagnetic indicators.

The concentration of blood glucose within the patient's capillary blood may be read directly from the disk 12 when dial 12 has been rotated to a null position. In FIG. 1, if the position of the dial 12 as shown represented a null position, the patient would directly read a blood glucose concentration of about 130 milligrams per milliliter.

The basic principles behind the meter 10 are well known. Early blood glucose measuring instruments, albeit table model versions, were manufactured using the basic analog circuit principles of meter 10 of the preferred embodiment. Lacking in those early blood glucose measuring instruments, and in any instruments thereafter, however, were the inexpensive means to calibrate test strip batch lot chemistry variations according to the present invention, such as calibration disk 14; the null prompting system of the present invention, as described; and the innovative circuitry to be described below that provides the null prompting system and other features of the invention also to be described below without the aid of a microprocessor.

Meter 10 of the preferred embodiment illustrated in FIGS. 1–8 utilizes the disposable test strips of the prior art that are provided with chemistries that produce a color change in proportion to the concentration of blood glucose within capillary blood applied to the chemistries. Meter 10 of this preferred embodiment is therefore provided with known optical reflectance circuitry to measure the blood glucose-induced color changes in the chemistries on the disposable test strips, and to generate a signal against which the analog circuit of the meter is balanced by means of the potentiometer varied with dial 12. Meter 10 could also be equipped with known circuitry to measure the change in electrical resistance of the disposable test strips of the prior art that have chemistries that change electrical resistance in proportion to the concentration of blood glucose in blood applied thereto.

Figure 7:
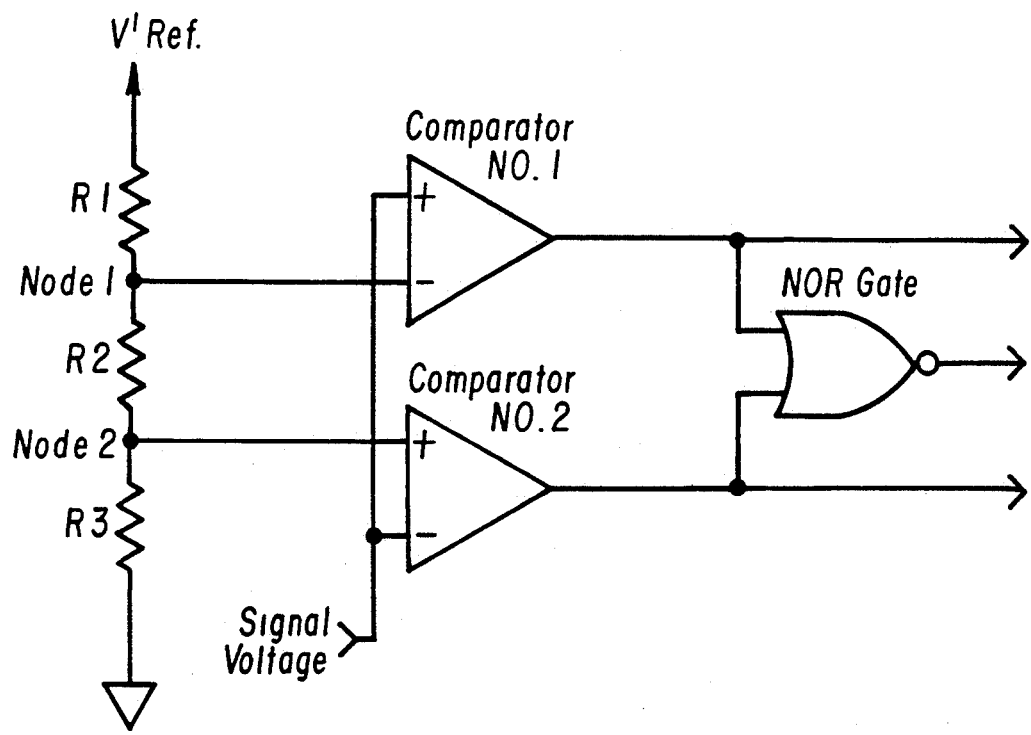
FIG. 7 is a circuit diagram showing the essential components of the non-linear null prompting system according to the invention.

Referring now to FIGS. 6 and 7, the null prompting system of meter 10 provides up to three null prompting signals for use in locating a null position. The three signals can be used in conjunction with indicator lights, such as the light emitting diodes that are indicating arrows 20 and 22 (FIG. 1), or the signals can be further modified, conventionally, for use with a liquid crystal display. The null prompting system of meter 10 allows the patient to trigger an indicator, such as arrows 20 and 22, when the calibration dial is high of the null position, lower than the null position, or within a given reference band representing the null position (FIG. 6). The use of such a non-linear null prompting system allows the patient to improve the resolution of the meter 10 at the high glucose concentration end of the calibration disk 14.

FIG. 7 is a circuit diagram showing the essential components the null prompting system of the invention. Three resistors $R_1$, $R_2$, and $R_3$ are used. One resistor, $R_1$, is variable. Two voltage levels are derived from the resistor string. The Reference Voltage, $V'_{ref}$ at Node 1 is compared with a Signal Voltage using Comparator #1. The Reference Voltage at Node 2 is compared with the same Signal Voltage using Comparator #2. If the Reference Voltage at Node 1 is less that the Signal Voltage, then Comparator #1 outputs a high signal. This indicates that the null position reference band is below the Signal Voltage level. Comparator #2 outputs a high signal if the Reference Voltage at node 2 is greater than the Signal Voltage. This indicates that the null position reference band is above the Signal Voltage level. The outputs of comparator #1 and comparator #2 are input into a NOR gate, which is high if the Signal Voltage is both less than the Reference Voltage at Node 1 and greater than the Reference Voltage at node 2. This indicates that the Signal Voltage is within the reference band and that a null position has been reached.

Figure 8:
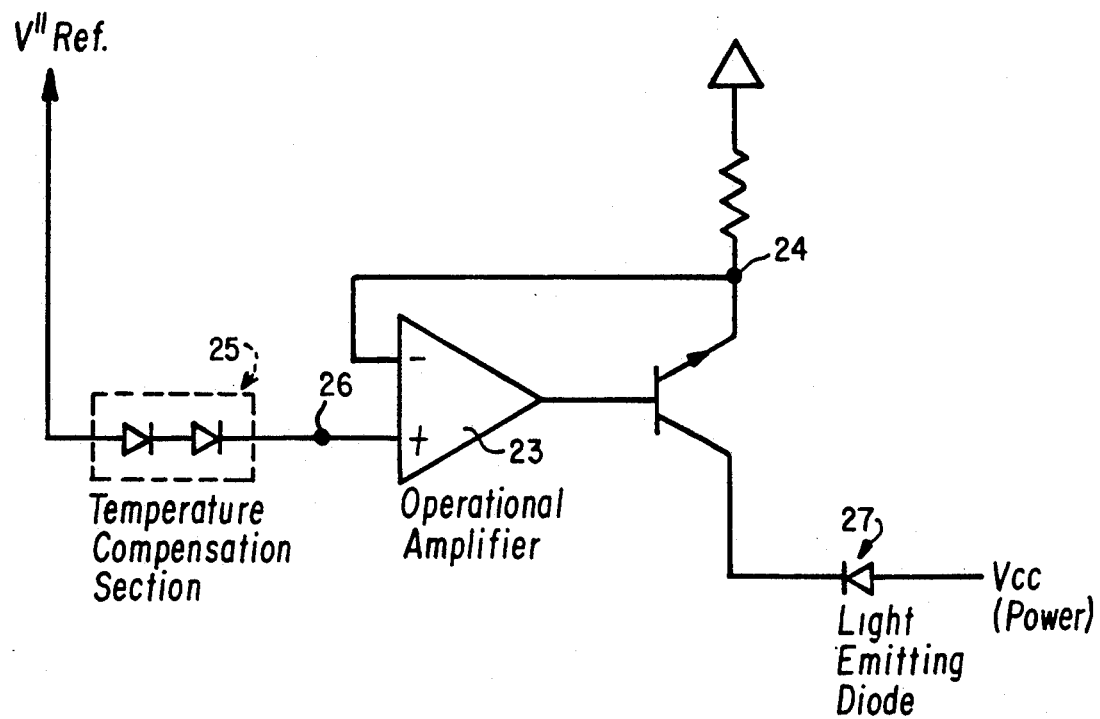
FIG. 8 is a circuit diagram showing the essential components of the temperature compensation scheme according to the invention.
Figure 11:
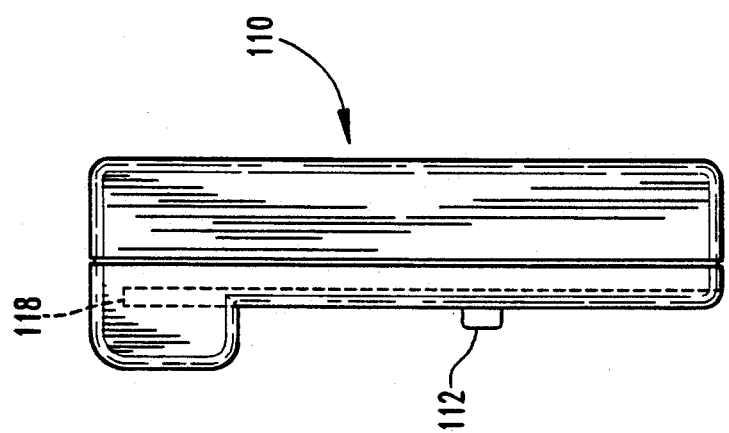
FIG. 11 is a right side view of the portable blood glucose monitoring meter of FIG. 9 without a test strip therein.

The preferred light source of the analog electronics used for the reflectance measuring system utilized in meter 10 is a light emitting diode 27 (FIG. 8). Heretofore, the change in light emitting diode brightness with temperature in optical reflectance measuring systems has required compensation by scaling with a known color standard and calculations with a microprocessor. The temperature compensation scheme for the light emitting diode 27 of the optical reflectance measuring system of meter 10 uses diodes in conjunction with an amplifier and a reference voltage to achieve a constant light emitting diode 27 brightness for the reflectance measuring system even when the temperature is not constant. By selecting the number and type of diodes, and the reference voltage, one can compensate for the decrease in brightness when the temperature increases for a variety of different light emitting diodes. Diodes have been used for temperature compensation in a variety of circuits, however, they have not been used in a portable instrument such as meter 10 that uses a light emitting diode 27 as the light source for a reflectance measuring system.

FIGS. 8 illustrates the temperature compensation scheme of the preferred embodiment. The feedback of an operational amplifier 23 causes the voltage at point 24 to be equal to the voltage at point 26. This voltage is equal to the Reference Voltage, $V''_{ref}$, minus the voltage drop across the Temperature Compensation Section 25, which may consist of one or more diodes in series. In general, the brightness of a light emitting diode 27 decreases with increasing temperature. The Temperature Compensation Section's voltage drop must therefore decrease with increasing temperature. This causes the voltage at point 24 to increase with increasing temperature, which compensates for the loss in brightness of a light emitting diode 27 by supplying the light emitting diode with more current.

Figure 12:
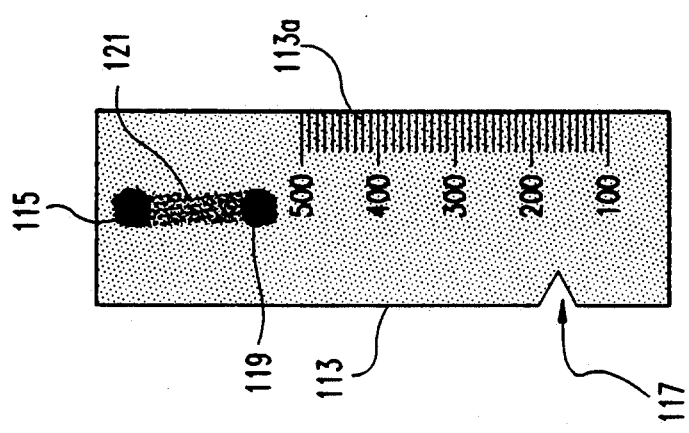
FIG. 12 is a top plan view of a preferred embodiment of a test strip with man-readable, individually calibrated blood glucose concentrations printed thereon that are calibrated to the chemistries of the strip for use with the portable blood glucose monitoring meter of FIG. 9.

Referring now to FIGS. 9–12, there is illustrated another preferred embodiment of the invention, a portable glucose monitoring meter 110. Meter 110 also employs an analog circuit, but in this preferred embodiment the analog circuit is utilized in conjunction with a sliding pointer 112, moveable along track 111, to vary the resistance of a potentiometer to balance the measure of the blood glucose-induced changes in the chemistries of the disposable test strips to be utilized in meter 110. In this embodiment, contrasted with the embodiment of FIGS. 1–9, man-readable, individually calibrated blood glucose concentrations 113a in milligrams per milliliter of blood are printed or impressed in a graduated scale format directly upon the disposable test strips themselves, as illustrated by test strip 113 in FIG. 12. The numbers appearing on the face of test strip 113 have been calibrated, by their exact positioning upon test strip 113, by empirical data to correspond to the specific batch lot variations in the chemistries that have been applied to test strip 113 at location 115. An individually calibrated graduated scale 113a would be created and applied to each test strip 113 by the test strip manufacturer in a position registered against a registration point on the test strip 113, such as notch 117 for example. A calibrated scale 113a would be created for each chemistry batch lot by testing test strips 113 from each batch lot with a meter 110 to locate null positions at reference blood glucose concentrations. Each test strip 113 manufactured with chemistries from the same batch lot would then have an identical calibrated scale 113a printed or impressed directly upon the face of the test strip 113 as illustrated in FIG. 12 in identical registration with registration point (notch) 117.

Figure 9:
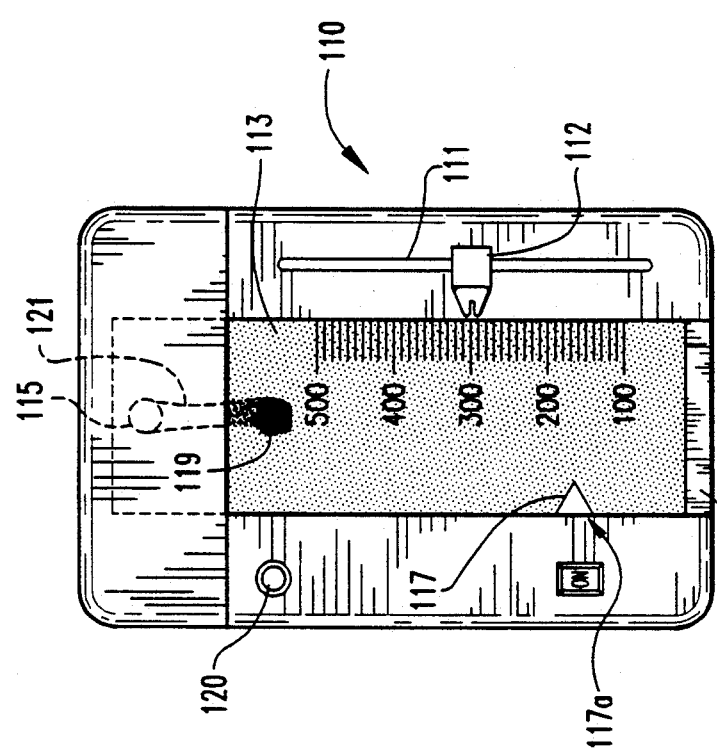
FIG. 9 is a top plan view of another embodiment of a portable blood glucose monitoring meter of a preferred embodiment of the invention.

Meter 110 is provided with slot means 118 to slideably receive test strip 113 in the manner illustrated in FIG. 9. Prior to the insertion of test strip 113 into meter 110, a drop of the patient's capillary blood is applied to sample application area 119, and the blood then moves by capillary action from area 119, along capillary action means 121, to sample reading area 115, where the patient's capillary blood interacts with the chemistries of test strip 113. Test strip 113 is then inserted into meter 110 and is latched into a registered position by a spring-biased locating means 117a, which corresponds with registration point (notch) 117 on the test strip 113. When in registered position within meter 110, calibrated scale 113a is in a registered juxtaposition with sliding pointer 112, and its track 111, thereby assuring properly calibrated readings of blood glucose concentration in the capillary blood sample applied to test strip 113.

The patient then moves sliding pointer 112 along track 111 until a null position is reached. At the null position, an indicator light 120 may be illuminated. The concentration of blood glucose within the patient's capillary blood may then be read directly from calibrated scale 113a of the test strip 113 opposite sliding pointer 112. In FIG. 9, if the position of sliding pointer 112, as illustrated, represented a null position, the patient would directly read a blood glucose concentration of about 270 milligrams per milliliter.

Figure 10:
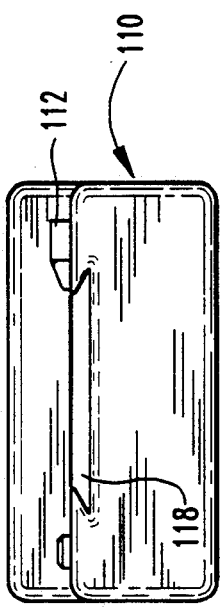
FIG. 10 is a front elevational view of the portable blood glucose monitoring meter of FIG. 9.

As was the case with meter 10 of FIGS. 1–9, the basic analog circuit principles of meter 110 of FIGS. 9–10 are also well known. The test strips 113 utilized in the preferred embodiment of meter 110 illustrated in FIGS. 9–12 are provided with chemistries of the prior art that produce a color change in proportion to the concentration of blood glucose within capillary blood applied to the chemistries. Meter 110 is therefore also provided with known optical reflectance circuitry to measure the blood glucose-induced color changes in the chemistries on test strips 113 at location 115, and to generate a signal against which the circuit is balanced by means of the potentiometer varied with sliding pointer 112. As was the case with meter 10, meter 110 could also be equipped with known circuitry to measure the change in electrical resistance of chemistries applied to test strips 113 at location 115 that change their electrical resistance in proportion to the concentration of blood glucose in the patient's capillary blood applied to the chemistries.

The temperature compensation scheme described above for meter 10 of the preferred embodiment illustrated in FIGS. 1–9 would also be applicable to the light source of the analog electronics used for the reflectance measuring system utilized in the preferred embodiment of meter 110. Similarly, the null prompting system described above for meter 10 would also be applicable to meter 110.

One of the advantages of meter 110 shared with meter 10 is that meter 110 can be made more cheaply than meters of the prior art since the microprocessor electronics associated with translating any electronically encoded calibration information are eliminated. Another major advantage of meter 110 is there is no question whether calibration information has been correctly entered into the meter. In every other known prior art meter, the data must either be entered with a key pad, a bar-code reading device, or an electronic memory module. Even meter 10 requires the patient to replace calibration disks 14, 14' with every new package of prior art test strips. All of these systems suffer the disadvantage that there is no guarantee that the user will, in fact, enter the calibration data into or onto the meter, or that the user will enter the data correctly. Thus this is an opportunity for the meter to be providing incorrect calibration information from a previously used batch of disposable test strips. There has been no fail-safe means to insure that the chemistry batch lot-specific information will be utilized correctly in the meter.

With meter 110, there is no necessity to enter calibration data by any means, either into or onto the meter since the individually calibrated scale 113a, specific to the batch-lot chemistries from which the strip is derived, has been printed or impressed directly on the strip during the manufacturing process. Means 117 and 117a are provided to insure that the test strip 113 must be inserted in a precise registered position within meter 110 in order for the meter 110 to function. Therefore, there can be no question that the patient will be reading blood chemistry concentrations calibrated to the individual chemistry of each strip 113.

Meter 110 could also be equipped with known circuitry to measure the change in electrical resistance of the disposable test strips of the prior art that have chemistries that change electrical resistance in proportion to the concentration of blood glucose in blood applied thereto.

The meters 10 and 110 of the preferred embodiments have been described as blood glucose monitoring meters. However, the meters 10 and 110 of the preferred embodiments can be easily adapted to be used with any enzyme-based blood analysis system, including cholesterol, for example, by selecting the appropriate chemistries to apply to the disposable test strips utilized with meters 10 and 110.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. In a portable blood glucose monitoring meter having an analog circuit with a variable potentiometer and a reflectance measuring system, including a light source, to measure blood glucose-induced color changes in the chemistries of disposable test strips to determine blood glucose concentrations, the improvements comprising:

a light emitting diode as the light source within said reflectance measuring system; and first circuit means connected to said light emitting diode for providing a current signal to said light emitting diode that varies in accordance with variations in ambient temperature to maintain a constant intensity brightness signal from said light emitting diode.

2. The meter of claim 1 wherein said first circuit means includes means for detecting a change in ambient temperature and producing a compensating signal in response thereto, and amplifier means responsive to said compensating signal for varying said current signal accordingly.

3. The meter of claim 2 wherein said means for detecting a change in ambient temperature includes at least one diode.

4. The meter of claim 3 wherein said amplifier means includes an operational amplifier and wherein at least one diode is forward biased with the cathode of said diode connected to an input of said operational amplifier, said amplifier means further including a transistor, said transistor connected in a feedback loop with said operational amplifier with the base of said transistor connected to the output of said operational amplifier, and wherein said transistor produced said current signal.

5. In a portable blood chemistry monitoring meter having an analog circuit with a variable potentiometer to measure blood chemistry-induced changes in an enzyme-based blood analysis system utilizing disposable test strips to determine blood chemistry concentrations, the improvements comprising:
   dial means to vary manually the resistance of said potentiometer to locate a null position that balances the measure of the blood chemistry-induced changes in the chemistries of the disposable test strips; and
   calibration means integral with said dial means to receive replaceable, pre-printed, man-readable blood chemistry concentrations that correspond to the null positions located by said dial means and that are empirically calibrated to the batch lot variations in the chemistries of the disposable test strips used in the meter.

6. The portable blood chemistry monitoring meter of claim 5 and further comprising null prompting means to indicate the manual variation of said dial means required to achieve a null position.

7. The portable blood chemistry monitoring meter of claim 5 wherein said dial means includes a manually rotatable dial.

8. The portable blood chemistry monitoring meter of claim 7 wherein said manually rotatable dial supports a replaceable, man-readable, pre-printed calibration disk.

9. The portable blood chemistry monitoring meter of claim 8 wherein said calibration disk displays man-readable blood chemistry concentrations about its periphery that are calibrated by their position about the periphery to the specific batch-lot chemistries applied to the disposable test strips to be used with the meter.

10. The portable blood chemistry monitoring meter of claim 5 wherein the enzyme-based blood analysis system is a blood glucose analysis system.

11. In a portable blood glucose monitoring meter having an analog circuit with a variable potentiometer to measure blood glucose-induced changes in the chemistries of disposable test strips to determine blood glucose concentrations, the improvements comprising:
   a sliding pointer with means to vary manually the resistance of the potentiometer to locate a null position that balances the measure of the blood glucose-induced changes in the chemistries of disposable test strips; and
   slot means to receive disposable test strips, the disposable test strips bearing calibration means that will be in registered juxtaposition with said sliding pointer when received by said slot means, said calibration means including man-readable blood glucose concentrations that correspond to the null positions located by said sliding pointer and that have been empirically calibrated to the batch lot variations in the chemistries of the disposable test strips.

12. The portable blood glucose monitoring meter of claim 11 wherein said analog circuit includes a reflectance measuring system having at least one light emitting diode and temperature compensation means to vary the current supplied to said light emitting diode as temperature varies to achieve constant light emitting diode brightness within the reflectance measuring system in the absence of a microprocessor.

13. In a portable blood chemistry monitoring meter having an analog circuit with a variable potentiometer to measure blood chemistry-induced changes in an enzyme-based blood analysis system utilizing disposable test strips to determine blood chemistry concentrations, the improvements comprising:
   a sliding pointer with means to vary manually the resistance of the potentiometer to locate a null position that balances the measure of the blood chemistry-induced changes in the chemistries of disposable test strips; and
   slot means to receive disposable test strips, the disposable test strips bearing calibration means that will be in registered juxtaposition with said sliding pointer when received by said slot means, said calibration means including man-readable blood chemistry concentrations that correspond to the null positions located by said sliding pointer and that have been empirically calibrated to the batch lot variations in the chemistries of the disposable test strips.

14. The portable blood chemistry monitoring meter of claim 13 wherein the enzyme-based blood analysis system is a blood glucose analysis system.

15. The portable blood chemistry monitoring meter of claim 13 wherein the enzyme-based blood analysis system is a blood cholesterol analysis system.

16. In a disposable test strip for a portable blood chemistry monitoring meter having an analog circuit with a variable potentiometer to measure blood chemistry-induced changes in an enzyme-based blood analysis system applied to the test strip to determine blood chemistry concentrations, the improvements comprising:
   calibration means to calibrate the batch lot variations in the chemistries of the enzyme-based blood analysis system in a man-readable format, said calibration means including pre-printed, man-readable blood chemistry concentrations registered directly on the test strip in positions corresponding to blood chemistry concentrations located by empirical testing with known blood chemistry concentrations.

17. The disposable test strip of claim 16 wherein the enzyme-based blood analysis system is a blood glucose analysis system.

18. The disposable test strip of claim 16 wherein the enzyme-based blood analysis system is a blood cholesterol analysis system.

* * * * *

UNITED STATES PATENT AND TRADEMARK OFFICE
CERTIFICATE OF CORRECTION

PATENT NO.    :    5,277,870

DATED         :    January 11, 1994

INVENTOR(S)   :    Maurice D. Fuller et al.

It is certified that error appears in the above-identified patent and that said Letters Patent is hereby corrected as shown below:

In column 3, line 44, change the word "hatch-lot" to -- batch-lot --.

Signed and Sealed this

Twenty-fourth Day of May, 1994

Attest:

BRUCE LEHMAN

Attesting Officer    Commissioner of Patents and Trademarks